United States Patent [19]

Sitek et al.

[11] 4,019,017
[45] Apr. 19, 1977

[54] ARC CONTROL CIRCUIT

[75] Inventors: George J. Sitek, Stevensville; Charles W. Berk, St. Joseph, both of Mich.

[73] Assignee: Leco Corporation, St. Joseph, Mich.

[22] Filed: Apr. 14, 1975

[21] Appl. No.: 567,930

[52] U.S. Cl. .............................. 219/135; 361/52
[51] Int. Cl.² ...................................... H02H 9/00
[58] Field of Search ...... 219/130, 136, 135, 131 R, 219/131 WR, 131 F; 356/36; 317/20; 323/9

[56] References Cited

UNITED STATES PATENTS

| | | | |
|---|---|---|---|
| 2,433,678 | 12/1947 | Tyrner | 219/135 |
| 2,617,913 | 11/1952 | Oestreicher | 219/135 |
| 3,141,085 | 7/1964 | Manz | 219/131 F |
| 3,627,977 | 12/1971 | Aldenhoff | 219/135 |
| 3,714,512 | 1/1973 | Grabowski | 323/9 |
| 3,791,743 | 2/1974 | Cody et al. | 356/36 |

*Primary Examiner* — J. V. Truhe
*Assistant Examiner* — Clifford C. Shaw
*Attorney, Agent, or Firm* — Price, Heneveld, Huizenga & Cooper

[57] ABSTRACT

An arc control circuit supplies voltage to an electrode of a portable analyzer for striking an arc against a specimen to provide an aerosol of the specimen material for analysis. The circuit includes a source of voltage and voltage dividing means for selectively applying different proportions of the source voltage to the electrode. Sensing means are coupled to the electrode for actuating bypass switching means coupled to the voltage dividing means when the electrode has made contact with the specimen to apply the full voltage of the power supply to the electrode to start the arc. As the electrode tip is withdrawn from the sample a predetermined distance, the desired arc is maintained. Means are provided for quenching the arc by opening the bypass switch to lower the electrode voltage once the arc has been maintained for a desired amount of time.

2 Claims, 1 Drawing Figure

ARC CONTROL CIRCUIT

BACKGROUND OF THE INVENTION

The present invention relates to an electrical circuit for supplying voltage to an electrode for starting, maintaining and quenching an arc between the electrode and a conductive member.

A portable manganese determinator in which a hand held probe utilizes an arc generating electrode when positioned against a specimen material is disclosed in U.S. Pat. No. 3,791,743 issued Feb. 12, 1974 to Thomas E. Cody et al. In such a system, an electrical arc is generated between the electrode and a conductive sample against which the probe is positioned vaporizing enough of the specimen for subsequent analysis by a flame photometer. In this system, a DC voltage is applied to the electrode which is moved into engagement with the surface of the specimen to be analyzed and subsequently backed off to a gap of approximately 1.2 mm to start and maintain the arc. The electrical circuit used for supplying the electrode power according to the teachings of this patent employs a constant current source and a delay circuit for controlling the amplitude and duration, respectively, of current applied to the electrode for controlling the arc.

Although such a system provides adequate results, the electrode is actuated by a voltage of about 50 V DC at all times and can be a shock hazard, particularly when the instrument is employed out of doors and in rainy or wet weather which occasionally occurs. This voltage, while sufficiently high to be a shock hazard is not high enough to sustain a good quality arc against many steels including, for example, stainless steel, with a relatively low conductivity.

SUMMARY OF THE INVENTION

The circuit of the present invention overcomes the deficiencies of the prior art by applying only a low voltage to the electrode except during actual arcing when the instrument is in use. Thus, the device constructed according to the present invention virtually eliminates any shock hazard. A relatively high voltage is applied to the electrode automatically when it has engaged a conductive specimen. The high voltage is sufficient to start and maintain a good quality arc on all types of conductive specimens including stainless and other steels.

The circuitry of the present invention includes means for alternately supplying an electrode with a relatively low voltage used for detecting electrical contact between the electrode and a conductive specimen and a relatively high voltage for generating the desired arc therebetween.

In one embodiment of the invention, a voltage source is coupled to an electrode by a voltage divider circuit and bypass switch means are coupled to the voltage divider. Detecting means are coupled to the electrode and to the bypass switch means for actuating said switch means to apply a higher voltage to the electrodes once contact with the specimen has been made. A control circuit is provided and also coupled to the switch means for lowering the voltage applied to the electrode after the arc has been sustained for the desired amount of time.

Thus, circuits embodying the present invention include means for application of two voltage levels to an electrode, one a low voltage which eliminates shock hazard and provides a voltage which can be utilized for detecting the contact between the electrode and the specimen and one a relatively high voltage for starting and maintaining the arc. Also, control means can be provided for quenching the arc after it has been maintained for a required amount of time.

These and other objects and purposes of the present invention and its operation, features and advantages, can best be understood upon reading the following description thereof together with the accompanying drawing in which:

DETAILED DESCRIPTION OF THE PREFERRED EMBODIMENT

Figure 1:
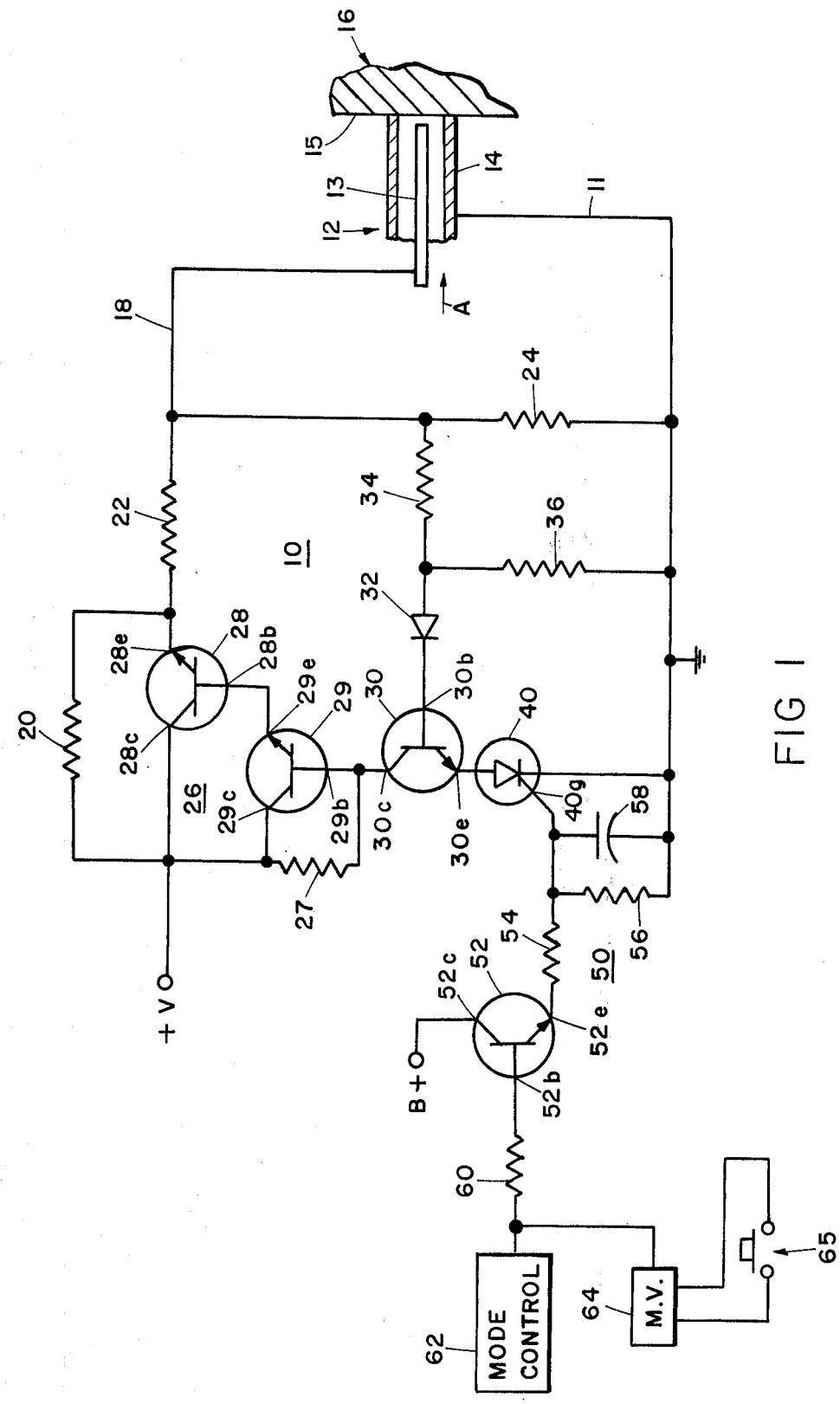
FIG. 1 is an electrical circuit diagram partly in block and schematic form of the circuitry of the preferred embodiment of the present invention and showing a probe used therewith in schematic form.

Referring now to FIG. 1, an electrical circuit 10 is coupled to a hand held probe 12 including an electrode 13 surrounded by a concentric collar 14 for providing mechanical and electrical coupling of the probe to the surface 15 of a specimen 16. Specimen 16 can be, for example, a billet of steel or other conductive material which includes an unidentified amount of an element such as manganese to be determined by a flame photometer or other analyzing instrument (not shown) coupled to probe 12. For purposes of the present invention, only the electrode and collar portions of the probe need be shown. The detailed construction of the entire probe 12 can be substantially identical to that disclosed in U.S. Pat. No. 3,791,743 identified above and incorporated herein by reference. Both the electrode 13 and surrounding collar 14 are made of a conductive material such as copper or an alloy thereof for providing electrical conduction between circuit 10 and specimen 16 which is likewise conductive. Electrode 13 is coupled to suitable mechanical means for momentarily advancing the tip of the electrode into engagement with surface 15 of the specimen as shown by arrow A. The means can include bias means mechanically coupled to the electrode for subsequently retracting the tip of the electrode to the position illustrated in the FIGURE once the arc is started to maintain a gap of approximately 1 mm to sustain the arc in conjunction with circuit 10. This arc vaporizes a sufficient amount of the specimen into a gaseous state which can be aspirated from the probe to the analyzer through a suitable conduit.

Circuit 10 supplies first and second level voltages applied between the electrode and specimen by conductors 11 and 18. Conductor 11, comprising the ground return of circuit 10, is coupled to collar 14 which when abutted against surface 15 of the specimen, completes the conduction path between conductors 11 and 18 when electrode 13 is in conductive relationship with the specimen. It is noted here that conductor 11 may instead be directly coupled to the specimen 15 by use of, for example, an alligator clip or the like. Collar 14, however, provides the preferred construction for providing a reference position for the electrode as well as continuous electrical contact between the circuit and the specimen. The collar also shields the operator from the electrode when in an operating position with high voltage applied thereto. In the preferred embodiment, collar 14 includes a plurality of magnets spaced around the periphery thereof for holding the probe against a ferromagnetic specimen once positioned in contact therewith.

Circuit 10 includes a relatively high voltage source +V which is approximately 100 V DC and which is coupled to electrode 13 via a voltage dividing network consisting of series coupled resistors 20, 22 and 24. Resistor 24 has a resistance of approximately one-tenth that of the sum of resistors 20 and 22 such that the voltage applied to the electrode from the +V source via the voltage divider is normally relatively low (i.e., 7 V DC). Resistor 22 likewise has a resistance which is insignificant as compared to the value of resistor 20.

Selectively bypassing resistor 20 is switch means 26 comprising a Darlington amplifier consisting of a first NPN transistor 28 having a collector terminal 28c coupled to the +V supply, an emitter terminal 28e coupled to the junction of resistors 20 and 22, and a base terminal 28b coupled to an emitter terminal 29e of a second NPN transistor 29 of the Darlington amplifier. Collector terminal 29c of transistor 29 is also coupled to the +V supply and base terminal 29b is coupled to ground through detection and control means including transistor 30 and an SCR 40. A bias resistor 27 couples the collector and base terminals of transistor 29.

With switch means 26 in the normally "off" position, a relatively low voltage is applied to electrode 13 from the +V supply through the voltage divider. When, however, the Darlington amplifier is rendered conductive by means of the detecting means or control circuit as described below, the relatively large resistor 20 is bypassed by the collector-to-emitter current path of transistor 28 to increase the voltage at electrode 13 to a relatively high voltage (approximately 100 V) for initiating and maintaining the arc.

The detection means comprises NPN transistor 30 having a base terminal 30b coupled to the junction of resistors 22 and 24 by means of a diode 32 and series coupled resistor 34. The junction of diode 32 and resistor 34 is coupled to ground by means of resistor 36. Diode 32 and the voltage dividers 34, 36 assure that transistor 30, normally forwardly biased for conduction, will be cut off when the voltage across resistor 24 momentarily approaches zero as electrode 13 initially contacts the specimen. The emitter terminal 30e of transistor 30 is coupled to the anode of an SCR 40 having its cathode coupled to ground. The gate terminal 40g of SCR 40 is coupled to a trigger circuit 50 including transistor 52 having a collector terminal 52c coupled to a source of power B+. The emitter terminal 52e of transistor 52 is coupled to gate 40g by means of current limiting resistor 54. A parallel RC network consisting of resistor 56 and capacitor 58 is coupled from gate 40g to ground. An input resistor 60 is coupled from the base terminal 52b of transistor 52 to a mode control circuit 62.

Circuit 62 is associated with the analyzer with which the probe is employed for generating a positive signal applied to the base of transistor 52 for rendering it conductive in turn actuating SCR 40 to terminate the arc as described below under OPERATION. The trigger signal from circuit 62 is generated in the preferred embodiment once a predetermined level of detected signal has been achieved indicating the arc has vaporized the specimen for a sufficient period to provide an accurate sampling. Circuit 62 thus includes a conventional comparator circuit and reference source therefor to provide the desired positive output signal.

Also coupled to the base of transistor 52 is a monostable multivibrator circuit 64 triggered by a push button reset switch 65.

OPERATION

Initially, as power is applied to circuit 10, multivibrator 64 applies a positive signal to the base of transistor 52 rendering it conductive and in turn applying a positive voltage to the gate of SCR 40. Transistor 30 is biased in a forward direction by the positive voltage across resistor 24 such that both transistor 30 and SCR 40 are conductive to lower the voltage on the base of transistor 29. Thus, transistor 29 and transistor 28 are rendered nonconductive to in effect open the switching means 26 causing the lower voltage to be applied by the voltage divider circuit to the electrode 13. As the operator is prepared to utilize the determinator, he pushes button 65 to reset the multivibrator 64 and remove the positive signal from transistor 52. SCR 40, however, being rendered conductive, continues to conduct and the voltage on electrode 13 remains low.

Once the probe is positioned against the surface of the specimen, as shown in the FIGURE, the electrode is mechanically advanced into momentary engagement with the surface thereby momentarily shorting out conductors 11 and 18. This momentarily lowers the voltage applied to the base of transistor 30 sufficiently to turn off the transistor, interrupting the current path through SCR 40 which in turn is rendered nonconductive. With transistor 30 and SCR 40 nonconductive, base terminal 29b is driven upwardly by the voltage from the +V source through resistor 27 rendering transistors 29 and 28 conductive to bypass resistor 20. When this occurs, the voltage applied to electrode 13 is increased to approximately 100 V thereby starting the arcing action simultaneously with the mechanical withdrawal of the electrode from the surface to an approximate distance of 1 mm. The arc is maintained until the mode control comparator detects a predetermined signal level as discussed above at which time it applies a positive voltage to the base 52b of transistor 52 which in turn triggers SCR 40 into conduction. It is noted that prior to this time, transistor 30 is biased in a forward mode of conduction but does not conduct due to the nonconductive SCR in the emitter circuit. With SCR 40 triggered, the base of transistor 20 is again returned to near ground potential cutting off transistors 29 and 28 and lowering the voltage at the electrode 13 to approximately 10 V or less quenching the arc. If additional samples are desired, the cycle can be repeated automatically by merely advancing electrode 13 into engagement with the specimen to momentarily short conductors 11 and 18 to repeat the cycle of operation of the circuit.

In the preferred embodiment, the following parameters were employed:

| Element | Number | Value |
|---|---|---|
| Resistor | 20 | 10 KΩ |
| " | 22 | 20 Ω |
| " | 24 | 1 KΩ |
| " | 27 | 5.6 KΩ |
| " | 34 | 2 KΩ |
| " | 36 | 500 Ω |
| " | 54 | 1.5 KΩ |
| " | 56 | 100 Ω |
| " | 60 | 20 KΩ |
| Capacitor | 58 | .1 MFD |
| Voltage Source | +V | +100 V DC |

-continued

| Element | Number | Value |
| --- | --- | --- |
| Voltage Source | B+ | +15 V DC |

It will become apparent to those skilled in the art that various modifications to the preferred embodiment shown herein can be employed. Such modifications may include the utilization of different circuit means for providing first and second level voltages automatically to the electrode in response to the electrode engagement with the specimen. Current sensitive means may be employed to control the application of such voltages and other forms of control circuits could be employed for quenching the arc once initiated. These and other modifications of the preferred embodiment will, however, fall within the spirit and scope of the present invention as defined by the appended claims.

The embodiments of the invention in which an exclusive property or privilege is claimed are defined as follows:

1. An electrical circuit for providing a low voltage to an electrode used for striking an arc against a conductive member and for providing a higher arc sustaining voltage to said electrode only when said electrode is in an arcing position in conductive relationship with a conductive work piece, said circuit comprising:
   a pair of output conductors for supplying electrical power to an electrode and a work piece;
   a source of direct voltage;
   voltage dividing means including first and second serially coupled resistors wherein said first resistor has an end remote from said second resistor coupled to said source and said second resistor is coupled between said output conductors for providing an output voltage between said conductors lower than the voltage of said source;
   solid state switching means for selectively bypassing at least a portion of said voltage dividing means to increase the voltage applied to said output conductors;
   detection means coupled to said output conductors and to said solid state switching means for actuating said solid state switching means to bypass said voltage dividing means when said output conductors are momentarily shorted by an electrode engaging a work piece, said solid state switching means comprising a first transistor having base, collector and emitter terminals wherein said base terminal is coupled to said detecting means and said first resistor is coupled between said collector and emitter terminals such that said first resistor is bypassed when said transistor is conductive and said detection means comprising a second transistor having base, collector and emitter terminals wherein said base terminal is coupled to one of said output conductors and one of said collector or emitter terminals is coupled to said base terminal of said first transistor, and means for coupling the remaining one of said collector or emitter terminals to the other of said output conductors such that voltage between said output conductors from said source forward biases said second transistor, and wherein said coupling means comprises an SCR having an anode-to-cathode current path coupled between said second transistor and said other output conductor and a gate terminal coupled to means for providing a control signal to trigger said SCR.

2. For use in an instrument employing a probe to engage a conductive specimen to vaporize a portion of the specimen for providing an aerosol sample for analysis; an electrical circuit for providing a low voltage to an electrode associated with the probe and used for striking an arc against the conductive specimen and for providing a higher arc generating and sustaining voltage to said electrode only when said electrode is in conductive relationship with a conductive specimen, said circuit comprising:
   a voltage source of relatively high direct voltage;
   an electrode;
   a first solid state switch and conductors coupling said voltage source to said electrode, said solid state switch including a control terminal for receiving signals for controlling the conduction of said solid state switch;
   a first resistor coupled in parallel to said solid state switch;
   a second resistor having a resistance about one-tenth the resistance of said first resistor, said second resistor coupled between said electrode and a specimen;
   a transistor having base, collector and emitter terminals, wherein the emitter to collector current path of said transistor is coupled to said control terminal of said solid state switch, and said base terminal is coupled to said electrode such that when said electrode engages a specimen said transistor is rendered non-conductive to actuate said solid state switch to bypass said first resistor to increase the voltage applied to said electrode by said voltage source;
   a control circuit for generating an enabling signal; and
   an SCR having an anode to cathode current path coupled in series with the emitter to collector current path of said transistor, and a gate coupled to said control circuit for receiving an enabling signal from said control circuit for actuating said SCR into conduction, said control circuit including a reset switch for removing the enabling signal applied to said gate of said SCR.

* * * * *